(12) United States Patent
Nerzak et al.

(10) Patent No.: US 10,197,533 B2
(45) Date of Patent: Feb. 5, 2019

(54) MEASURING DEVICE

(71) Applicant: SMS group GmbH, Duesseldorf (DE)

(72) Inventors: Thomas Nerzak, Moenchengladbach (DE); Hermann Josef Klingen, Moenchengladbach (DE); Guido Sonnenschein, Moenchengladbach (DE); Thomas Daube, Moenchengladbach (DE); Eduard Stecklein, Moenchengladbach (DE)

(73) Assignee: SMS group GmbH, Duesseldorf (DE)

( * ) Notice: Subject to any disclaimer, the term of this patent is extended or adjusted under 35 U.S.C. 154(b) by 129 days.

(21) Appl. No.: 15/207,566

(22) Filed: Jul. 12, 2016

(65) Prior Publication Data
US 2017/0016857 A1    Jan. 19, 2017

(30) Foreign Application Priority Data

Jul. 13, 2015  (DE) .................. 10 2015 111 278
Nov. 12, 2015  (DE) .................. 10 2015 119 548

(51) Int. Cl.
G01N 27/90   (2006.01)
B21B 38/04   (2006.01)
H01F 27/10   (2006.01)

(52) U.S. Cl.
CPC .......... G01N 27/9026 (2013.01); *B21B 38/04* (2013.01); *H01F 27/10* (2013.01)

(58) Field of Classification Search
CPC .... G01N 27/72; G01N 27/9046; G01R 33/12; G01R 33/1223; G01V 3/107
USPC ................................. 324/239, 240
See application file for complete search history.

(56) References Cited

U.S. PATENT DOCUMENTS

| | | |
|---|---|---|
| 3,586,967 A | 6/1971 | Peyrot et al. |
| 4,024,470 A | 5/1977 | Vild et al. |
| 4,461,995 A * | 7/1984 | Harris ................ G01N 27/9006 165/47 |
| 4,629,991 A | 12/1986 | Wheeler |
| 4,810,988 A | 3/1989 | Schenk, Jr. et al. |
| 4,862,079 A | 8/1989 | Chickering et al. |
| 5,130,653 A | 7/1992 | Wu et al. |

(Continued)

FOREIGN PATENT DOCUMENTS

| | | |
|---|---|---|
| CN | 103148775 A | 6/2013 |
| DE | 198 50 055 C1 | 5/2000 |

(Continued)

OTHER PUBLICATIONS

British Office Action in GB 1612027.1, dated Dec. 14, 2016.
(Continued)

*Primary Examiner* — Jermele M Hollington
*Assistant Examiner* — Suresh K Rajaputra
(74) *Attorney, Agent, or Firm* — Collard & Roe, P.C.

(57) ABSTRACT

A measuring device that is able to function even in rough environments, for example under great heat or in environments in which water or steam is found, as is the case in rolling mills, among other environments, has a housing, a central measuring device that passes through the housing in a straight line, and a measuring coil that is disposed in the housing and encloses the measuring opening. The device has a coil carrier that is disposed in the housing radially outside of the measuring coil and carries the measuring coil.

21 Claims, 1 Drawing Sheet

(56) References Cited

U.S. PATENT DOCUMENTS 5,638,000 A  6/1997  Foerster
6,617,849 B1  9/2003  Scharlemann

FOREIGN PATENT DOCUMENTS

| EP | 0 078 672 A1 | 5/1983 |
| EP | 0 468 905 A1 | 1/1992 |
| EP | 2 115 449 B1 | 11/2009 |
| EP | 2 366 474 A1 | 9/2011 |
| FR | 2 532 208 A1 | 3/1984 |
| JP | S54-12790 A | 1/1979 |
| JP | S61747 A | 1/1986 |
| WO | 00/77513 A1 | 12/2000 |

OTHER PUBLICATIONS

Austrian Office Action in A 323/2016-1,2, dated Jul. 19, 2017, with English translation of relevant parts.
British Office Action in GB 1612027.1, dated Jun. 9, 2017.
Spanish Search Report in ES 201630954, dated Jul. 13, 2016, with English translation of relevant parts.
German Office Action dated May 25, 2016 in German Application No. 10 2015 119 548.8 with English translation of relevant parts.

\* cited by examiner

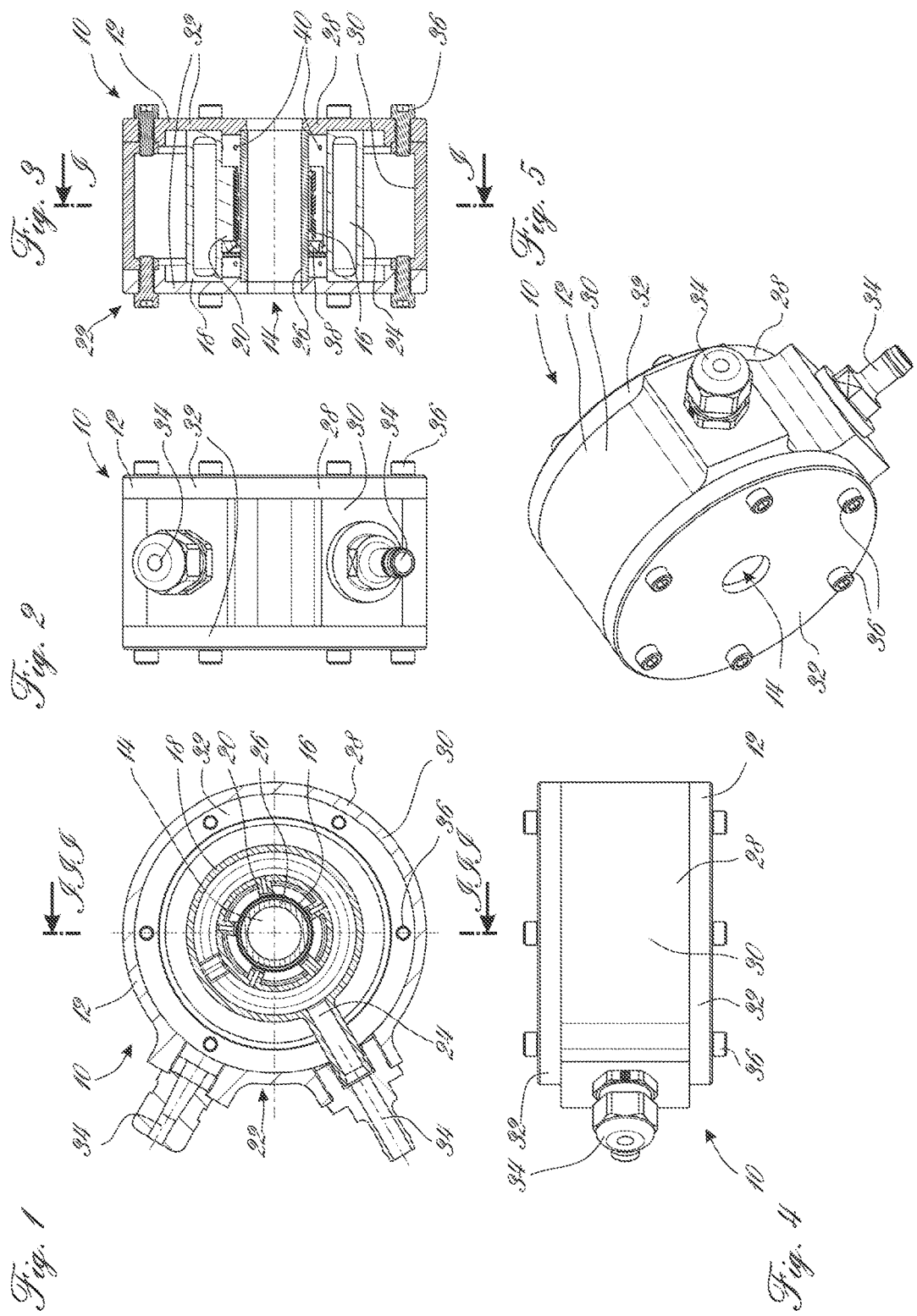

MEASURING DEVICE

CROSS REFERENCE TO RELATED APPLICATIONS

Applicant claims priority under 35 U.S.C. § 119 of German Application No. 10 2015 111 278.7 filed Jul. 13, 2015 and from German Application No. 10 2015 119 548.8 filed Nov. 12, 2015, the disclosures of which are incorporated by reference.

BACKGROUND OF THE INVENTION

1. Field of the Invention

The invention relates to a measuring device having a housing and having a central measuring opening that passes through the housing in a straight line, and having a measuring coil that is disposed in the housing and encloses the measuring opening.

2. Description of the Related Art

Such arrangements are commercially available as ring coils, for example. They serve for detecting changes in cross-section of a work piece that runs axially through the measuring opening, for example, by a change in inductivity or, alternatively, by eddy current measurements, for example, in that two measuring coils, one for inducting the eddy currents and one for detecting the eddy currents, are installed accordingly. U.S. Pat. No. 4,862,079 also discloses a corresponding arrangement, wherein here, the measuring coil appears to be mounted in the housing. An arrangement having movable measuring coils that support themselves, which are carried, by two laterally disposed bolts that allow mobility, is disclosed, by U.S. Pat. No. 5,638,000.

SUMMARY OF THE INVENTION

It is the task of the present invention to make available a measuring device of the type stated, which is able to function even in rough environments, for example under great heat or in environments in which water or steam is found, as is the case in rolling mills, among other environments.

The task is accomplished by means of a measuring device according to the invention. Further advantageous embodiments, possibly also independent of this aspect, are discussed below.

Thus, a measuring device having a housing, having a central measuring opening that passes through the housing in a straight line, and having a measuring coil that is disposed in the housing and encloses the measuring opening, can be used in a rough environment if it is characterized by a coil carrier that is disposed, in the housing radially outside of the measuring coil and carries the measuring coil. Thermally caused expansion of the measuring coil, for example on the basis of a high work piece temperature or on the basis of a high ambient temperature, then leads to the result that the expanding measuring coil does not depart from the coil carrier because of its heat expansion. Rather, the expanding measuring coil continues to be reliably carried by the carrier and to be precisely positioned.

This embodiment makes it possible for the measuring device to be positioned even particularly between the roll stands of a rolling mill, for example, or in the immediate vicinity of a corresponding roll stand, so that it becomes possible to detect the cross-section of the respective work piece very shortly behind or ahead of the roll stands, using measuring technology, and—if necessary—to act on the rolling process in controlling or regulating manner.

Depending on the concrete embodiment of the measuring coil, if applicable also using multiple measuring coils, the cross-sectional surfaces of non-ferromagnetic materials can be detected accordingly, and this feature particularly also holds true for materials that do not demonstrate ferromagnetic properties at high temperatures or pressures, as is the case, for example, for steel under the operating conditions that exist in a rolling mill.

Preferably, the coil carrier is fixed in place in the housing, so that reliable positioning not only of the coil carrier but also of the measuring coils carried by it, in each instance, can be guaranteed under all operating conditions of the measuring device. This reliable positioning can particularly be guaranteed in that the coil carrier is clamped in place, because possible thermally caused expansions or shrinkages can be counteracted by means of a suitable selection of the tension, in that a suitable bias is selected. If necessary, possible cooling effects or other cooling media that have an expanding or contracting effect on the coil carrier are also taken into consideration with regard to the bias or the type of fixation.

It is understood that—if necessary—one or more further coil carriers can also be provided supplementally, for example a coil carrier that lies radially on the inside, which carriers particularly serve for installation purposes and from which the measuring coil can lift up at higher temperatures, if necessary. On the other hand, because the danger exists that such a coil carrier merely has a disruptive effect during operation of the measuring device, it appears advantageous to remove such a coil carrier that lies on the inside.

If the measuring coil lies against the coil carrier radially on the inside, then carrying of the measuring coil can be guaranteed in very simple and operationally reliable manner, in terms of construction, even if the measuring coil expands on the basis of thermal stress, because this expansion merely leads to an even more intimate connection between measuring coil and coil carrier.

It is understood that although the position of the measuring coil should be fixed in place as much as possible by the coil carrier, certain relative movements between measuring coil and coil carrier can certainly take place. Thus, it is conceivable, for example, that the measuring coil tilts slightly in order to follow thermally related forces, but this tilting is generally only of subordinate importance with regard to measuring precision.

Preferably, the coil carrier has supports that face radially inward and carry the measuring coil or against which the measuring coil lies. This arrangement facilitates installation, because in this way, the interior of the coil carrier in which the measuring coil is disposed becomes more easily accessible. Furthermore, the measuring coil thereby provides the possibility of being able to work within the coil carrier, wherein the width of the supports, in other words the contact surface of the supports with the measuring coil, is selected in such a manner that a sufficient carrying surface or sufficient stability for the measuring coil is guaranteed. Also, it is conceivable that cooling fluid can flow past the supports or is guided past them, and in this way—if necessary—direct cooling of the measuring coil can take place.

Preferably, the coil carrier is composed of non-electrically-conductive or weakly electrically conductive material, in order to reduce an interaction with the measuring coil or an impairment of the measured result to a minimum. In this regard, it is understood that the extent of the electrical conductivity is selected as a function of the desired measuring precision or as a function of a possible impairment of the measured results, as long as this precision or impairment can still be tolerated.

Thus, the coil carrier can also be formed from plastic, for example, particularly if suitable cooling is provided. Likewise, ceramics, in particular, are also conceivable as materials for the coil carrier.

In order to reduce the thermal stress of the entire arrangement, it is advantageous if a cooling system is provided.

The cooling system can particularly comprise a cooling fluid, which allows particularly effective cooling. Preferably, the cooling system comprises a flowing cooling fluid, because in this way, possible local hot spots of the cooling fluid, which cannot be transported away in suitable manner, can be reduced to a minimum.

Water or air are particular possibilities as cooling fluids, particularly because in general, corresponding media are sufficiently available in rolling mills and similar facilities in any case, because they guarantee good cooling in the case of a suitable embodiment of the cooling system, and because in general, they can be controlled well in terms of the construction and their physical properties. It is understood that—if necessary—other cooling fluids, such as oils, emulsions, inert gases or the like, for example, can also be used.

In particular, it is advantageous if the coil carrier is operatively connected with the cooling system, because on the one hand, this connection can guarantee good cooling of the coil carrier itself, particularly if the coil carrier is formed from plastic and has modules composed of plastic.

In the case of a suitable design of the cooling system, it is particularly easily possible to guarantee that thermal expansion of the coil carrier remains below thermal expansion of the measuring coil at the given operating conditions of the measuring device, so that, the measuring coil is carried by the coil carrier or lies against it in operationally reliable manner under all the operating conditions.

In particular, the cooling system can comprise at least one guide channel for the cooling fluid. If necessary, it can be prevented by means of a suitably equipped guide channel that the cooling fluid gets, into the immediate vicinity of the measuring coil and, in particular, also into interior of the measuring coil, and possibly distorts the measured result. Likewise, however, it is also conceivable to guide cooling fluid to the measuring coil in targeted manner, particularly also into the interior of the measuring coil or to other locations, by means of the guide channel.

In particularly is advantageous if the guide channel for the cooling fluid is disposed in or on the coil carrier; this arrangement allows targeted cooling of the coil carrier, with the advantages already mentioned above, on the one hand, and, on the other hand, if the guide channel is closed toward the measuring coil, can ensure that the cooling fluid does not directly flow around the measuring coil and get into its interior. Also, in the case of a suitable embodiment, a particularly compact construction is obtained, because then, the coil carrier can serve not only its coil-carrying function but also for guidance of coolant, so that the total arrangement has a particularly compact construction.

In this regard, it is advantageous if the guide channel reaches all the way into the supports, so that the most extensive cooling possible of the measuring coil, on the one hand, and of the coil carrier, on the other hand, can be guaranteed in the region of the supports.

In particular, cooling with a cooling fluid proves to foe suitable if the measuring device must meet very great demands, particularly great thermal demands, as is the case, for example, in the immediate vicinity of the roll stands or within a rolling mill, and between the individual roll stands.

The cooling system is preferably configured in such a manner that the cooling fluid flows directly past the measuring coil. This flow preferably takes place cumulatively to cooling of the coil carrier or to a guide channel disposed in or on the coil carrier, and the resulting cooling of the measuring coil. On the other hand, this flow can also take place alternatively to the latter, if the latter does not appear necessary, for example.

In particular, it can be advantageous if the cooling fluid flows past the measuring coil radially on the inside, because the heat stress caused by the work piece to be measured also takes place radially from the inside.

In general, the measuring coil will comprise not just a bare wire that is correspondingly wound into a coil, but rather a correspondingly insulated wire. Likewise, it is conceivable that the wire that essentially makes up the measuring coil is stabilized to form a coil body, by means of suitable measures; this stabilization can take place, for example, by embedding the wire in plastic or also by means of a slightly thicker and cohesively configured insulation. By having cooling fluid flow past, the measuring coil directive, a slightly more sensitive measuring coil, particularly having a slightly more sensitively structured coil corpus, which cannot withstand great heat because of the insulation used, for example, can also be used.

In particular, if the fluid flows past the measuring coil not just radially on the inside, but also radially on the outside, next to the supports, flow around the measuring coil can be achieved, and this arrangement guarantees particularly intensive cooling.

For protection of the measuring coil, particularly against thermal stress, for example if freshly rolled work pieces pass through the measuring opening, it is advantageous if a heat shield is disposed radially within the measuring coil.

Preferably, this heat shield is composed of non-electrically-conductive or weakly electrically conductive material, particularly of a material that has the lowest possible influence on magnetic fields, in order to have little influence on the fields that are used for the measurement. Here, too, the extent of the electrical conductivity is selected as a function of the desired measurement precision or as a function of a possible impairment of the measured results, as long as this precision or impairment can still be tolerated.

In order to fulfill the task as a heat shield as well as possible, it is advantageous if this heat shield is formed from ceramic materials that can withstand correspondingly high temperatures. If necessary, plastics are also conceivable, if these plastics can also withstand correspondingly high temperatures and are suitably cooled.

Preferably, the heat shield is configured in such a manner that it also protects the measuring coil against other adverse influences, such as, for example, against particles that split off, which come off the work piece, or against direct contact with very hot steam or the like. For this purpose, it is particularly advantageous if the heat shield closes off the housing radially on the inside.

The heat shield can be integrated into the measuring device in structurally simple manner, if it is clamped in place by the remaining housing or by a remaining housing wall, so that thermal expansions can also foe easily countered, if the bias values are selected in suitable manner.

It is particularly advantageous if the cooling system is configured in such a manner that the cooling fluid flows against the heat shield or past it. This arrangement brings about particularly intensive cooling of the heat shield, which relieves stress on the heat shield itself, on the one hand, and, on the other hand, also correspondingly reduces the heat given off by the heat shield to other modules of the measuring device, such as, for example, to the measuring coil, to the remaining housing, or to the coil carrier.

If the guide channel of the cooling system opens into the housing interior, the cooling system can be distributed within the measuring device in intensive and targeted manner by way of the opening or by way of the openings. In particular, the cooling fluid can then be applied to the heat shield by way of the opening or the openings, and can act there directly and in targeted manner. Likewise, it is possible to direct the cooling fluid into an interstice between measuring coil and heat shield, and the opening or openings can also be used for this purpose. This arrangement also then guarantees, in advantageous manner, that the cooling fluid can flow directly past the heat shield or can flow directly past the measuring coil. Accordingly, it is advantageous if an opening or openings of the guide channel is or are directed at the heat shield, at the measuring coil (16) and/or at an interstice between measuring coil and heat shield. It is understood that in the case of multiple openings, the openings can be directed at different modules or into different regions.

The housing of the measuring devices can preferably be closed and can have a housing wall that—if applicable—also covers the heat shield.

Preferably, the housing wall, with the exception of the components that lie within the measuring coil, such as, for example, the heat shield, is configured to be metallic or composed of conductive material, so that the housing shields the measuring coil or the interior of the central measuring opening against electromagnetic radiation. This shielding particularly holds true, of course, for possible influences from the outside that distort the measured result, but also for the occurrence of possible errors that can be caused by the measuring coil and the measurement.

Preferably, the housing wall of the housing has at least one passage for operating means for the cooling fluid mentioned above or electrical lines, particularly as feed, lines for the measuring coil, so that the measuring device as a whole is represented, as a compact, structural unit and can be used quickly and in operationally reliable manner, under adverse ambient conditions, as is the case in rolling mills, for example.

It is understood that the characteristics of the solutions described above and in the following description can also be combined, if necessary, in order to be able to implement the advantages cumulatively, accordingly.

BRIEF DESCRIPTION OF THE DRAWINGS

Further advantages, goals, and properties of the present invention will be explained using the following description of an exemplary embodiment, which is also particularly shown in the attached drawing. The drawing shows:

FIG. 1 shows a measuring device in section along the line I-I from FIG. 3;

FIG. 2 is a side view of the measuring device according to FIG. 1;

FIG. 3 shows the measuring device according to FIGS. 1 and 2 in section along the line III-III in FIG. 1;

FIG. 4 shows the measuring device according to FIGS. 1 to 3 in a top view; and FIG. 5 is a perspective view of the measuring device according to FIGS. 1 to 4.

DETAILED DESCRIPTION OF PREFERRED EMBODIMENTS

The measuring device 10 shown in the figures comprises a housing 12 that in turn has a housing wall 28 that comprises a housing ring 30 and two housing lids 32, which are connected with screws 36 (numbered as an example), in each instance.

In this regard, the housing lids 32 have openings, in each instance, so that a measuring opening 14 remains in the measuring device 10, through which opening a work piece, not shown, can pass through the measuring device 10 or within which opening a tool, not shown, can be disposed.

The housing 12 furthermore comprises a heat shield 26 that encloses the measuring opening 14, lying radially on the inside, and is clamped in place by the housing lids 32, wherein here—if necessary—a different fastening possibility can be provided. In this exemplary embodiment, the heat shield 26 is configured to be cylindrical and corresponds to the geometric arrangement of the two openings of the housing lids 32 in terms of its geometry, so that accordingly, a measuring opening 14 having a cylindrical geometry also exists. It is understood that in other embodiments, other cross-sectional shapes can also be provided, if necessary.

A measuring coil 16 is disposed radially outside of the heat shield 26 and within the housing 12; this coil encloses the measuring opening 14 and is carried by a coil carrier 18.

The coil carrier 18 has supports 20 (numbered as an example) that face radially inward, against which supports the measuring coil 16 lies, so that thermally related expansion of the measuring coil 16 leads to the result that the measuring coil 16 continues to lie against the coil carrier 18 and is carried by it.

For installation purposes, a securing ring 38 (FIG. 3) is disposed axially on one side of the supports 20; in the present exemplary embodiment, this ring is formed from the same material as the coil carrier 18 itself, wherein in other embodiments, other material, can also be selected, if necessary. This arrangement makes it possible to push the measuring coil 16 onto the supports 20, in that the securing ring 38 is first taken off. After this pushing on takes place, the securing ring 38 can be set on again, and in this manner, the measuring coil 16 can be securely positioned.

The coil carrier 18 itself is clamped into the housing 12 by way of the housing lids 32, wherein here, of course, other types, such as, for example, glued connections or screwed connections or the like can be provided in deviating embodiments.

The measuring device 10 furthermore comprises a cooling system 22 that particularly comprises a guide channel 24 for feeding in air as a cooling fluid. This guide channel 24 is configured in the coil carrier 18, on the one hand, and reaches all the way into the supports 20, so that very good cooling of the coil carrier 18, in particular, but also of the measuring coil 16 can be guaranteed. Also, the guide channel 24 is connected with a passage 34 through the housing wall 28, so that the air feed can be guaranteed in simple and operationally reliable manner.

Radially on the inside, the guide channel 24 has openings 40 shown in FIG. 3 that are directed directly at the heat shield 26 in this exemplary embodiment, and can cool this shield in this manner, in that air or cooling fluid is caused to flow onto the heat shield 26. The air or cooling fluid can then also get into the interior of the measuring coil 16 and thereby flow past the heat shield 26 and the measuring coil. The same holds true for the interstice between coil carrier 18 and measuring coil 16 laterally relative to the supports 20. It is understood that in deviating embodiments, the openings 40 can also be provided at a different location and with a different orientation. For example, the openings 40 can also be disposed in such a manner that cooling fluid is directed directly into the corresponding interstices between measuring coil 16 and heat shield 26 or measuring coil 16 and coil carrier 18. In particular, openings 40 can also be oriented differently.

In this exemplary embodiment, the air then escapes through the naturally existing gaps of the housing 12, wherein in this way, the interior of the housing 12 stands under excess pressure. In other embodiments, a supplemental passage for escape of the air can also be provided.

The housing 12 furthermore has a further passage 34 for electrical lines. In this exemplary embodiment, however, this passage is sealed, so that only minimal air, if any, can escape from the pressurized interior of the housing 12 through this passage 34. In a deviating embodiment, however, it is possible to do without a seal here, if necessary, so that the air can primarily leave the housing 12 through this passage 34. Likewise, it is possible, in a deviating embodiment, to provide bores or outlet nozzles in the housing wall 28, for example particularly in the housing lids 32 or even in the heat shield 26, through which the air or another cooling fluid can leave the housing 12, wherein it can then be used for cooling the work piece or other modules, for example, if these bores or outlet nozzles are directed at the work piece or the other modules, for example, or, in particular, if they are directed in the rolling direction if they are provided in the housing lid 32 that lies in the back, in the rolling direction.

In other embodiments, water, for example, or a different cooling liquid can be used as a cooling fluid. Here, it does not appear very practicable to do without a passage that serves as an outlet. Accordingly, it is advantageous to provide the passage 34 that is used for electrical lines or also a supplemental passage as an outlet, and this arrangement then allows a cooling fluid circuit. If necessary, the bores or outlet nozzles provided in the housing wall 28 and described, above can also be used, but because then guiding the respective cooling fluid in a circuit does not appear possible, this arrangement leads to a corresponding loss of cooling fluid, which loss should, however, be accepted in view of the supplemental function.

Likewise, it is conceivable to do without the openings 40, for example, if direct cooling of the measuring coil 16 or of the heat shield 26 does not appear necessary. Then, in particular, the guide channel 24 can be provided with an outlet that is connected with a further passage, so that good flow of cooling fluid, particularly of cooling liquid through the coil carrier 18 or through the cooling system 22 can be guaranteed.

Although the housing wall 28 is configured to be metallic, in order to serve as a shield against electromagnetic radiation, the heat shield 26 is configured from non-conductive material, in this exemplary embodiment from ceramic, so that on the one hand, it represents good heat protection for the measuring coil 16, and itself demonstrates great heat resistance, and on the other hand impairs the magnetic fields as little as possible.

In this exemplary embodiment, the coil carrier 18 is configured from non-conductive material, so that it impairs the magnetic fields as little as possible. In the present exemplary embodiment, plastic is backed in the selection of the material for the coil carrier 18, because this material is cost-advantageous and can be cooled well and sufficiently by way of the cooling system 22. In deviating exemplary embodiments, other materials, for example ceramic, can also be used.

The measuring device 10 is also suitable for use in rolling mills—and there, in particular, also between roll stands or in their immediate vicinity. Thus, the measuring device 10 can particularly also detect steel as a work piece directly, using measuring technology, because steel is not ferromagnetic at rolling temperatures. Accordingly, the measuring device 10 can particularly be used for monitoring cross-section. If necessary, speed measurements or measurements of a mass through-flow or the like can be measured using a measuring device structured accordingly in terms of its measuring coil 16, wherein this structure ultimately depends on the configuration of the measuring coil 16, for example also in the form of multiple measuring coils, and on the signal processing as well as the control of the measuring coil 16.

Although only a few embodiments of the present invention have been shown and described, it is to be understood that many changes and modifications may be made thereunto without departing from the spirit and scope of the invention.

What is claimed is:

1. A measuring device comprising:
   (a) a housing;
   (b) a central measuring opening passing through the housing in a straight line;
   (c) a measuring coil disposed in the housing concentric with and enclosing the central measuring opening; and
   (d) a coil carrier disposed in the housing radially outside of the measuring coil and carrying the measuring coil, wherein the coil carrier has supports that face radially inward and carry the measuring coil.

2. The measuring device according to claim 1, wherein the coil carrier is fixed in place in the housing.

3. The measuring device according to claim 1, wherein the coil carrier is clamped in place in the housing.

4. The measuring device according to claim 1, wherein the measuring coil lies against the coil carrier radially from the inside.

5. The measuring device according to claim 1, further comprising a cooling system that comprises a flowing cooling fluid.

6. The measuring device according to claim 5, wherein the cooling fluid comprises water or air.

7. The measuring device according to claim 5, wherein the cooling system comprises at least one guide channel for the cooling fluid.

8. The measuring device according to claim 7, wherein the at least one guide channel is disposed in or on the coil carrier.

9. The measuring device according to claim 7, wherein the guide channel reaches all the way into the supports.

10. The measuring device according to claim 5, wherein the cooling system is configured so that the cooling fluid flows past the measuring coil directly.

11. The measuring device according to claim 10, wherein the cooling fluid flows past the measuring coil radially on the inside.

12. The measuring device according to claim 7, further comprising a heat shield disposed radially within the measuring coil.

13. The measuring device according to claim 12, wherein the heat shield closes off the housing radially on the inside.

14. The measuring device according to claim 12, wherein the cooling system is configured so that the cooling fluid flows against or past the heat shield.

15. The measuring device according to claim 7, wherein the at least one guide channel opens into a housing interior of the housing.

16. The measuring device according to claim 15, wherein the at least one guide channel opens radially inward.

17. The measuring device according to claim 12, wherein the at least one guide channel has at least one opening located at or directed toward at least one of the heat shield, the measuring coil, and an interstice between the measuring coil and the heat shield.

18. The measuring device according to claim 1, wherein the housing is closed off and a housing wall of the housing has at least one passage for an operating device.

19. The measuring device according to claim 18, wherein the operating device comprises cooling fluid or electrical lines.

20. A measuring device comprising:
(a) a housing;
(b) a central measuring opening passing through the housing in a straight line;
(c) a measuring coil disposed in the housing concentric with and enclosing the central measuring opening; and
(d) a coil carrier disposed in the housing radially outside of the measuring coil and carrying the measuring coil, wherein the coil carrier is composed of non-electrically conductive or weakly electrically conductive material.

21. A measuring device comprising:
(a) a housing;
(b) a central measuring opening passing through the housing in a straight line;
(c) a measuring coil disposed in the housing concentric with and enclosing the central measuring opening; and
(d) a coil carrier disposed in the housing radially outside of the measuring coil and carrying the measuring coil, wherein the coil carrier is made of ceramic.

* * * * *